US00PP31285P2

(12) United States Plant Patent
Hansen

(10) Patent No.: US PP31,285 P2
(45) Date of Patent: Dec. 24, 2019

(54) ***SALVIA* PLANT NAMED 'SWEET PETITE'**

(50) Latin Name: *Salvia pratensis*
Varietal Denomination: Sweet Petite

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,938

(22) Filed: Feb. 1, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

*Primary Examiner* — Kent L Bell

(57) ABSTRACT

The new and distinct cultivar of perennial *Salvia* plant named 'Sweet Petite' characterized by its very large lavender-pink flowers from dark rosy-red buds, densely arranged in verticils. The new plant has a short, compact habit with stiff, upright, heavily-branched stems and a strong vigorous growth rate and gray-green foliage. 'Sweet Petite' is useful for landscaping as a specimen plant or en masse.

1 Drawing Sheet

Botanical denomination: *Salvia pratensis.*
Cultivar designation: 'Sweet Petite'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Salvia* 'Sweet Petite' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Sweet Petite' or as the new plant. The new plant was selected from a block of seedlings resulting from an open pollination in late spring of 2013 with the unreleased, proprietary hybrid known as 12-23-09 as the female or seed parent and the male parent is unknown but may have been any sage from a large number of other hybrids and selected cultivars within the breeding area of a wholesale perennial nursery in Zeeland, Mich., USA. Seed was collected in the summer of 2013 and sown at the same nursery. The new plant was initially evaluated in the summer of 2015 and assigned the breeder code 13-40-1 through the trial process.

The new *Salvia* was further evaluated and asexually propagated initially by division and later by basal cuttings taken at the same nursery in Zeeland, Mich., USA in 2015. Evaluation of these and further cutting grown plants shows that *Salvia* 'Sweet Petite' continues to be stable and produce true to type plants in successive generations of asexual propagation.

SUMMARY OF THE INVENTION

Plants of *Salvia* 'Sweet Petite' have not been observed under all possible environmental conditions. The phenotype may vary somewhat with variations in environment such as temperature, nutrition and light intensity without, however, any variance in genotype.

*Salvia* 'Sweet Petite' can be closely compared to *Salvia* 'Sweet 16' U.S. Plant Pat. No. 24,311, 'Ballerina Pink' U.S. Plant Pat. No. 29,957, 'Pretty in Pink' U.S. Plant Pat. No. 29,550 and *Salvia* 'Pink Dawn' U.S. Plant Pat. No. 26,343. 'Sweet 16' flowers for a shorter season on taller and broader plants. 'Ballerina Pink' has softer, lighter pink flowers on slightly taller plants. 'Pretty in Pink' has more vibrant lavender-pink flowers on slightly larger plants. The stems and calyxes of 'Pink Dawn' are much darker pigmented with greyed-purple than the new plant, the flowers are darker, deep, purplish pink and the habit is taller than the new plant. The female parent, 12-23-09 is taller in habit and has flowers of a different hue. Further comparison with the female parent is not possible as it was not maintained.

The following characteristics in combination distinguish Saliva 'Sweet Petite' as a new and distinct cultivar from all other cultivars known to the inventor:

1. Very large lavender pink flowers densely arranged in verticils;
2. Stiff, upright, heavily-branched stems;
3. Dark rosy-red flower buds;
4. Short, compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Sweet Petite'.

The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed.

DETAILED BOTANICAL DESCRIPTION

Figure 1:
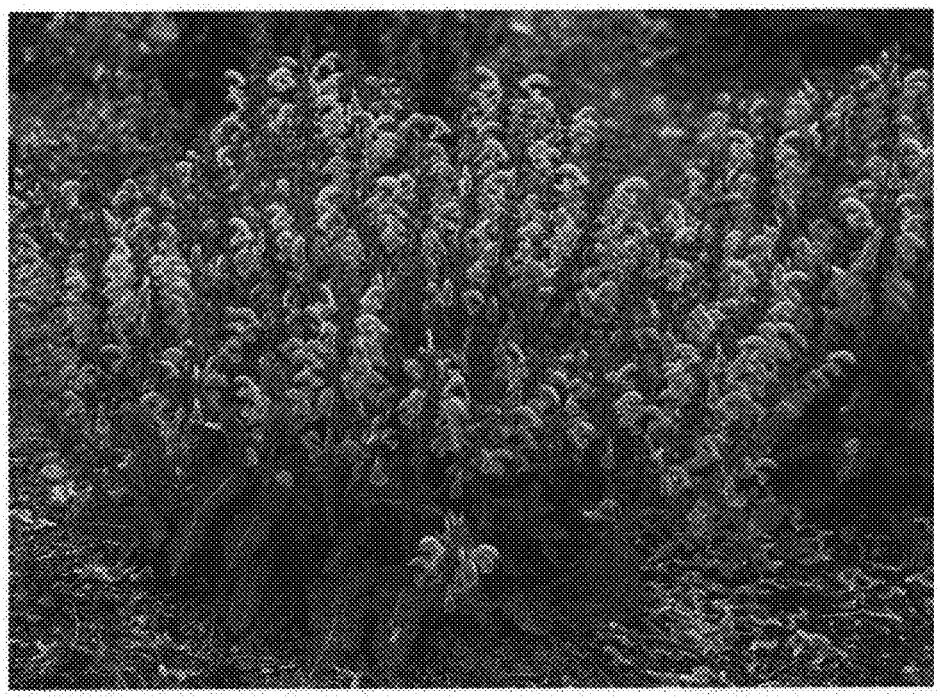
FIG. 1 shows the plant habit in full flower in a landscape.
Figure 2:
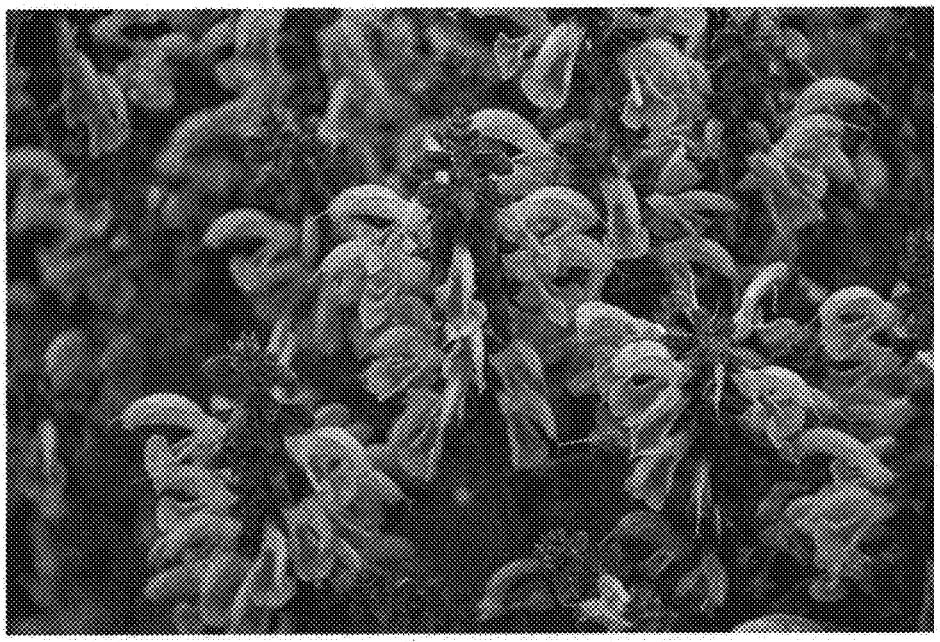
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Sweet Petite' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. and greenhouse forced two-year old plants. Plants were given supplemental water and fertilizer and plant growth regulators were used for the greenhouse trials only.

Botanical Classification: *Salvia pratensis* (Linnaeus);

Parentage: Female or seed parent proprietary hybrid 12-23-09; unknown male or pollen parent;

Plant habit: Winter-hardy herbaceous perennial; multi-stemmed, compact, rounded, with mostly basal foliage, and flowers in several tightly arranged verticils on branched upright racemes displayed above foliage; in flower with panicles about 40 cm tall and about 55 cm wide at the fullest point; cauline foliage extends up the stems about 20 cm and 48 cm wide;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks Root description: Fine, well-branched; color dependent on age and soil type, from cream to dark tan in color;

Foliage: Opposite, simple, rugose, lanceolate; margin crenulate; glabrous and matte abaxial and adaxial surfaces; acute apex and base cordate to auriculate with lobes frequently overlapping; leaf blades about 12.5 cm long and 6.5 cm across, decreasing in size distally; average about 9.0 cm long and 5.0 cm across; faint sage fragrance;

Foliage color: Adaxial surface between RHS 138A and RHS 138B; abaxial surface nearest RHS 146B;

Venation: Reticulate; impressed on adaxial side and costate on abaxial side; pubescent abaxial, puberulent adaxial;

Vein color: Adaxial midrib nearest RHS 145C; adaxial primary and secondary veins nearest RHS 145C toward midrib and gradually darkening to nearest RHS 138A toward leaf margins; abaxial midrib nearest RHS 145C; abaxial primary veins nearest RHS 145C and secondary veins gradually darkening to nearest RHS 146C toward leaf margin;

Petiole: Concavo-convex; pubescent abaxial and along margin, sparsely puberulent adaxial; to about 5.5 cm long and 5.0 mm wide, average 3.5 cm long and 4.0 mm wide at base;

Petiole color: Adaxial and abaxial surfaces nearest 146D;

Flower description: Perfect, bilabiate, verticillate with flowering generally beginning at lower verticils and advancing up the scape, but not all flowers at each verticil opening at the same time giving the effect of a scape being in continuous flower for longer periods; average distance between verticils about 4.0 mm, greater proximally and less distally; attitude with midline projected about 10 degree angle above horizontal and hood petal about 45 degree angle above horizontal; self-cleaning, petals not persistent; flowering beginning late spring for about six weeks and repeating if initial scapes removed;

Flower longevity: About four days on the plant or as cut flower;

Flower fragrance: None detected under present growing conditions;

Flower buds one to two days prior to anthesis: Shape is rounded on top and slightly concave below, with rounded apex; pubescent; about 11.0 mm long, 5.0 mm tall and 3.0 mm wide;

Bud color: Exposed petals blend between RHS 67A and RHS N66A; abaxial calyx nearest RHS 146B with veins and blushing on dorsal portion nearest RHS 187B;

Flowers: Bilabiate corolla with arcuate hooded upper lip and tri-lobed lower lip; about 2.4 cm long, 14.0 mm tall and 8.0 mm wide fused into tube in the proximal 8.0 mm; clustered at verticils with about six flowers per verticil;

Petals: Bilabiate corolla; upper hood petal and flattened side to side vertically, with notched apex and base fused with labium;

Hood (upper) petal: Minutely pubescent outside, glabrous inside; about 20.0 mm long, 10.0 mm tall and 3.0 mm across;

Labium (lower) petal: Consisting of three lobes, two proximal lobes about 3.0 mm long and 3.0 mm wide at base with rounded apex; center lobe emarginate, about 5.0 mm long 7.0 mm wide with a 2.0 mm apical notch in middle; center lobe concaved upwards; total labium about 15.0 mm long, 8.0 mm wide at the widest portion across lobes and 5.0 mm tall;

Petal color: Abaxial and adaxial hood petal nearest RHS 75C; lower labium petal abaxial nearest RHS 75C and adaxial nearest RHS 75C distally and between RHS N74B and RHS N74C in central portion; fused basal 2.0 mm inside calyx nearest RHS NN155D;

Androecium: Two, fused with labium, contained within hood petal except when triggered by pollinator;

*Filament.*—Glabrous, fused about 7.0 mm from base of labium petal; curved around inside of hood petal; about 12.0 mm long and less than 0.5 mm diameter with a 2.0 mm trip mechanism at base; color of base nearest RHS 65C, distally nearest RHS N74D.

*Anther.*—Glabrous, oblong, about 3.0 mm long and 1.0 mm diameter; longitudinal, dorsifixed; color nearest RHS N187A.

*Pollen.*—Abundant; globose; less than 0.1 mm circumference; color nearest RHS 12A.

Gynoecium: One, curved around inside of hood petal;

*Style.*—About 24.0 mm long and less than 0.5 mm diameter; color nearest RHS NN155D at base, nearest RHS 65C near central portion and intensifying distally about 3.0 mm before stigma split to nearest RHS 73A.

*Stigma.*—Bifurcate and curved in the terminal 2.0 mm; apex pointed; color nearest RHS N74B. Ovary; superior; color more green than RHS 145A and more yellow than RHS 138B.

Fruit: Nutlet, one to four per flower; rounded, about 1.5 mm diameter; color darker than RHS 200A; Calyx; five sepals, three upper and two lower, campanulate, apex acute; fused in basal 4.0 mm; tube about 7.0 mm long and 6.0 mm tall at mouth and 3.0 mm wide; lower set bifurcate in terminal 2.5 mm; upper set of trifurcate in distal 1.0 mm; Calyx color; variable with light intensity, abaxial bases and regions in little direct sunlight nearest RHS 146B with veins of nearest RHS 138A, abaxial regions receiving more intense light developing veins nearest RHS 187A; adaxial between RHS 146D and RHS 146C with darker veins of RHS 137A toward apex;

Bracts: Each verticil subtended by two opposite nearly cordate bracts; apex acuminate, base truncate, margin entire and ciliolate; coarsely wavy to bent downward toward apex; margin minutely pubescent, and glabrous above and below; bract size up to 10.0 mm long and 6.0 mm wide, decreasing distally;

Bract color: Variable with light intensity, in less light abaxial and adaxial surfaces nearest RHS 146A with midrib and base nearest RHS 145C; color with more intense light nearest RHS N186C on both surfaces;

Peduncles: Raceme; quadrangular in base cross section; about 20 per plant; strong; upright; to about 40 cm tall and 4.5 mm across at base; puberulent to glandular; branches in lower two to four nodes, upright at 65 degrees above horizontal or greater; branches to about 18.0 cm long and 3.0 mm across at base; average internode distance about 2.0 cm;

Peduncle color: Nearest RHS 138A;

Pedicels: Cylindrical; puberulent to glandular; about 1.5 mm long and 0.5 mm diameter; puberulent to glandular; nearly horizontal at flower anthesis;

Pedicel color: Nearest RHS 146D;

Disease and pest resistance: Plants of *Salvia* 'Sweet Petite' perform best with adequate moisture and good drainage and are hardy from USDA zone 3 to 8. Resistant to diseases and pests beyond that common to *Salvia* has not been noted.

It is claimed:

1. The new and distinct perennial *Salvia* plant named 'Sweet Petite' as herein described and illustrated.

* * * * *